United States Patent [19]
Loewe et al.

[11] 3,984,561
[45] Oct. 5, 1976

[54] ANTHELMINTICALLY ACTIVE 2-CARBALKOXY-AMINO-BENZIMIDAZOLE-5(6)-PHENYL ETHERS AND METHOD FOR USING THE SAME

[75] Inventors: Heinz Loewe, Kelkheim, Taunus; Josef Urbanietz, Schwalbach, Taunus; Reinhard Kirsch; Dieter Düwel, both of Hofheim, Taunus, all of Germany

[73] Assignee: Hoechst Aktiengesellschaft, Frankfurt am Main, Germany

[22] Filed: Jan. 23, 1974

[21] Appl. No.: 435,771

Related U.S. Application Data

[62] Division of Ser. No. 318,271, Dec. 26, 1972, Pat. No. 3,954,791.

[30] Foreign Application Priority Data

Dec. 27, 1971  Germany............ 2164690

[52] U.S. Cl. ................................. 424/273
[51] Int. Cl.² ............................. A61K 31/415
[58] Field of Search ......................... 424/273

[56]  References Cited
UNITED STATES PATENTS 3,772,322  11/1973  Horlein et al.............. 424/273

Primary Examiner—Frederick E. Waddell
Attorney, Agent, or Firm—Curtis, Morris & Safford

[57]  ABSTRACT

2-Carbalkoxy-amino-benzimidazole-5(6)-phenyl ethers of the formula (I)

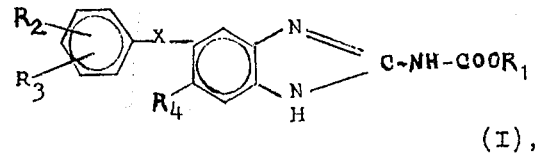

in which $R_1$ represents alkyl of 1 to 4 carbon atoms, $R_2$ and $R_3$ represent, independently of each other, hydrogen, hydroxyl, alkoxy of 1 to 4 carbon atoms, halogen, trifluoromethyl, alkyl of 1 to 4 carbon atoms or carbalkoxy of 1 to 4 carbon atoms in the alkoxy group, $R_4$ represents hydrogen or chlorine and X represents oxygen or sulfur as anthelmintically active compounds in pharmaceutical preparations and a method for using the same.

38 Claims, No Drawings

ANTHELMINTICALLY ACTIVE 2-CARBALKOXY-AMINO-BENZIMIDAZOLE-5(6)-PHENYL ETHERS AND METHOD FOR USING THE SAME

This is a division of application Ser. No. 318,271 filed Dec. 26, 1972, now U.S. Pat. No. 3,954,791 granted May 4, 1976.

2-Carbalkoxy-amino-benzimidazol derivatives with alkyl or acyl groups in 5(6) position are known to be anthelmintic agents (P. Actor et al., Nature 215, 321 (1967); DOS 2.029.637).

The present invention provides anthelmintically active 2-carbalkoxy-amino-benzimidazole-5(6)-phenyl ethers of the formula (I)

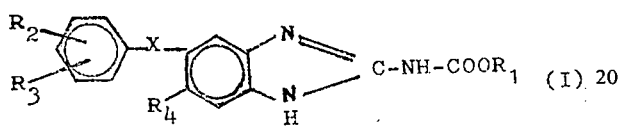

in which $R_1$ represents alkyl of 1 to 4 carbon atoms, $R_2$ and $R_3$, independently of each other, represent hydrogen, hydroxyl, alkoxy of 1 to 4 carbon atoms, halogen, trifluoromethyl, alkyl of 1 to 4 carbon atoms or carbalkoxy of 1 to 4 carbon atoms in the alkoxy radical, $R_4$ represents hydrogen or chlorine and X represents oxygen or sulfur. Compounds of the formula (I) in which $R_1$ represents methyl, $R_2$, $R_3$ and $R_4$ each represent hydrogen and X represents oxygen or sulfur are particularly preferred.

The alkyl groups in the substituents $R_1$, $R_2$ and $R_3$ may be methyl, ethyl, propyl, isopropyl, butyl, sec. butyl, tert. butyl. The alkoxy groups in the substituents $R_2$ and $R_3$ may be methoxy, ethoxy, propoxy, isopropoxy and butoxy. The halogen atoms in the substituents $R_2$ and $R_3$ may be fluorine, chlorine, bromine and iodine. The carbalkoxy groups in the substituents $R_2$ and $R_3$ may be carbomethoxy, carbopropoxy or carbobutoxy.

The present invention furthermore relates to a process for preparing 2-carbalkoxy-amino-benzimidazole-5(6)-phenyl ethers of the formula (I), in which $R_1$, $R_2$, $R_3$, $R_4$ and X have the meanings given above, wherein an o-phenylene-diamine of the formula (VII), in which $R_2$, $R_3$, $R_4$ and X have the same meaning as that given for formula (I), is condensed either a. with an alkyl-S-methyl-thiourea carboxylate of the formula (IV) in which $R_1$ has the same meaning as that given for formula (I), or b. with a cyanamide caboxylate of the formula (VI) in which $R_1$ has the same meaning as that given for formula (I), in a pH range of from 1 to 6, preferably from 2 to 5.

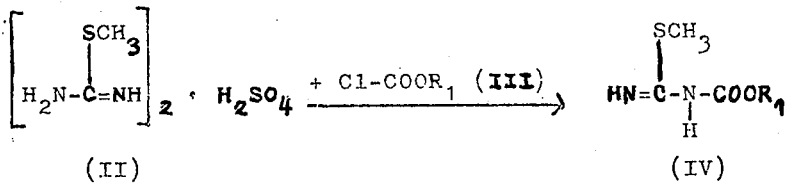

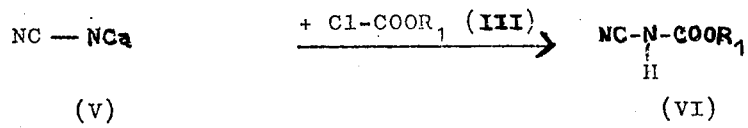

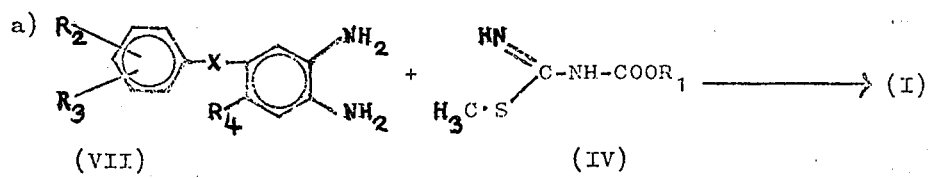

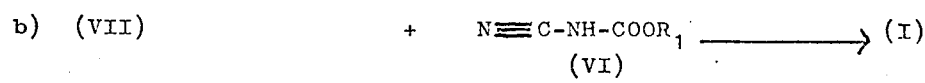

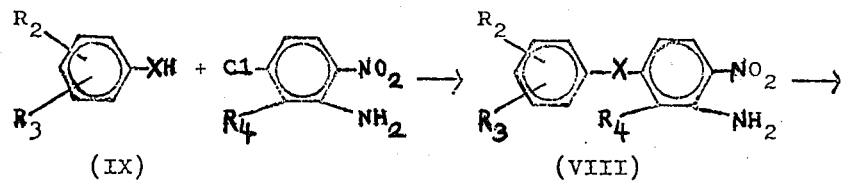

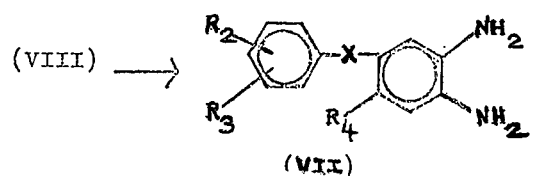

For carrying out the reaction according to method a), the S-methyl-thiourea sulfate of the formula (II) and a chloroformiate of the formula (III) in which $R_1$ has th same meaning as that given in formula (I), are mixed at first in water, a strong base, for example a 25% sodium hydroxide solution is added dropwise, while keeping the temperature low, preferably at 0° C. The alkyl-S-methyl-thio-urea carboxylate of the formula (IV) need not be isolated.

The pH-value of the reaction batch obtained as described above is then preferably adjusted to a value of between 2 and 5, suitably by adding an organic acid such as acetic acid or lactic acid. Then, the o-phenylene-diamine derivative of the formula (VII) is added, either in the form of a free base or as acid addition salt, for example as hydrochloride. In the last-mentioned case it may be advantageous to add an alkali metal salt of an organic acid as buffer. For the reaction of the reaction components, it is suitable to use a reaction temperature in the range of from 30° to 100° C; the duration of the reaction may be between 30 minutes and 10 hours. Methyl-mercaptan is set free as a side-product. Isolation of the 5(6)-phenoxy- or 5(6)-phenylmercapto-2-benzimidazole-carbaminates of the formula (I) is carried out in the usual manner, for example by diluting the reaction batch with water and filtering off the product that has separated.

For carrying out the reaction according to method b), a chloroformiate of the formula (III) is added to an aqueous suspension of cyanamide in the form of a salt, advantageously in the form of the calcium salt (V), while maintaining the reaction temperature at between 40° and 60° C by cooling. After separation by filtration of dark side products, the cyanamide carboxylate of the formula (VI) is obtained in the filtrate. The cyanamide carboxylate (VI) so obtained is combined with an o-phenylene-diamine derivative (VII) and the pH-value of the mixture is brought to a value of between 1 and 6, preferably 2 and 4, by addition of a mineral acid, for example concentrated hydrochloric acid. During the reaction, the reaction mixture is suitably kept at a temperature of between 30° and 100° C, depending on the reactivity of the o-phenylene-diamine derivative, for a period of time of 30 minutes to 10 hours. After having allowed the reaction mixture to cool, the reaction product (I) that has precipitatd is isolated by filtration and washing.

The o-phenylene-diamine derivative (VII) used as starting material is obtaind by reduction of a corresponding aminonitrodiphenyl ether of the formula (VIII) in which $R_2$, $R_3$, $R_4$ and X have the same meansings as those given in formula (I). The reduction may be effected, for example, by hydrogenation in the presence of Raney nickel and of a solvent such as methanol or dimethylformamide at temperatures in the range of from 20° to 60° C or by a treatment with reducing agents, for example with a solution of tin-(II)-chloride in glacial acetic acid saturatd with hydrochloric acid gas; in this case, the tin double salt of the o-phenylenediamine (VII) is first isolated, which is then decomposd by a treatment with a concentrated sodium hydroxide solution. The diamine thus set free is then dissolved in an organic solvent which is immiscible with water.

The o-phenylenediamine derivative (VII) can be reacted either as free amine in the manner indicated above with an alkyl-S-methylthiourea carboxylate (IV) or with a cyanamide-carboxylate (VI), or in the form of its acid addition salt with a suitable mineral or organic acid such as hydrochloric acid, sulfuric acid, acetic acid, oxalic acid or similar acids.

The amino-nitro-diphenyl ethers (VIII) are obtained by reaction of a phenol of the formula (IX), in which $R_2$ and $R_3$ and X have the same meaning as that given for formula (I), with 5-chloro-2-nitroaniline or, if they are compounds of the formula (VIII) in which $R_4$ stands for chlorine, with 4,5-dichloro-2-nitroaniline, suitably in the presence of agents having an alkaline reaction such as potassium carbonate, at temperatures between 80° C and the boiling temperature of the solvent used, within a period of time of half an hour up to 5 hours. Isolation is carried out by dilution of the reaction mixture with water and separation by filtration of the precipitate.

If in one of the amino-nitro-diphenyl ethers (VIII) $R_2$ or $R_3$ represents hydroxyl, such compounds of the formula (VIII) are used as starting substances in which $R_2$ or $R_3$ represents a methoxy group; these compounds are treated with an agent splitting off ether groups, for example with hydrobromic acid.

The 2-carbalkoxy-amino-benzimidazole-5(6)-phenyl ethers of the present invention are valuable chemotherapeutic agents and are suitable for combatting diseases caused by parasites in humans and animals.

They are particularly active against a great number of helminths, for example Haemonchus, Trichlostrongylus, Ostertagia, Strongyloides, Cooperia, Chabertia, Oesophagostomum, Hyostrongylus, Ankylostoma, Askaris and Heterakis. Particularly marked is the activity against gastro-intestinal Strongylides, which are above all infesting ruminants. The infestation of the animals by these parasites causes great economical damages, so that the compounds of the invention are mainly used in veterinary medicine.

The active substances according to the invention are administered together with suitable pharmaceutical solvents or carriers, perorally or subcutaneously, the one or the other form of administration being preferred in accordance with the prevailing circumstances.

The activity of the compounds of the invention was teted by chemotherapeutic experiments carried out on ewe-lambs having a weight of about 30 kg and which had been infested artificially with larvae of Haemonchus contortus or Trichostrongylus colubriformis. The test animals were kept in tiled stalls which were daily thoroughly cleaned. After termination of the prepatency period (time between infection and maturity of the parasites with beginning excretion of eggs or larvae), the number of eggs per gram of faeces was determined with the modified McMaster process according to Wetzel (Tierarztliche Umschau 6, 209 – 210 (1951)). Directly thereafter, the treatment of the sheep (in general 4 to 8 animals per active substance, at least however 2) was begun. The animals obtained perorally, in one case also subcutaneously, a suspension of 2.5 or 5 mg/kg of body weight in each time 10 ml of a 1 % tylose suspension. On the 7th, 14th and 28th day after the treatment, the number of eggs per gram of faeces was determined according to the above-indicated method and the percentual degree of decrease in comparison to the value determined before the begin of the treatment was calculated.

The following Table indicates the activity of the new substances of the invention determined according to the above-described method in comparison to two known compounds of similar structure; these compounds were Parbendazol (cf. P. Actor et al., Nature 215, 321 (1967); D. Ross, Veterinary Record 82. 731 (1968); D.R. Johns et al., Australian Veterinarian Journal 45. 460 (1969) and Mebendazol (DOS 2.029.637).

The novel active substances of the invention were designated as follows:

A = 5-phenoxy-benzimidazole-2-methyl-carbaminate

B = 5-(4-chloro-phenoxy)-benzimidazole-2-methyl-carbaminate

C = 5-(3-chloro-phenoxy)-benzimidazole-2-methyl-carbaminate

D = 5-(2-chloro-phenoxy)-benzimidazole-2-methyl-carbaminate

E = 5-(3-methoxy-phenoxy)-benzimidazole-2-methyl-carbaminate

F = 5-phenylmercapto-benzimidazole-2-methyl-carbaminate

The known active substances were designated as follows:

Comp. subst. 1 = Parbendazol
Comp. subst. 2 = Mebendazol

Table

| Active substance | Dos.cur.min. in mg/kg | Administration | Effect in % |
|---|---|---|---|
| A | 2.5 | peroral | 100 |
| B | 5.0 | peroral | 94 |
| C | 2.5 | peroral | 100 |
| D | 5.0 | peroral | 96 |
| E | 2.5 | peroral | 100 |
| F | 2.5 | peroral | 100 |
| F | 2.5 | subcutaneous | 100 |
| Comp. subst. 1 | 15.0 | peroral | 100 |
| Comp. subst. 2 | 10.0 | peroral | 76 – 100 |

As the Table shows, the new carbaminates of the invention are superior to known compounds of similar structure in that the Dosis curativa minima is essentially lower.

The Dosis tolerata maxima of the products of the invention is higher than 3200 mg/kg of body weight, upon peroral and subcutaneous administration.

The active substances of the formula I of the invention are administered, depending on the case, in doses ranging between 0.5 and 50 mg per kg of body weight for a period of 1 to 14 days.

For oral application, there may be used tablets, dragees, capsules, powders, granulates or pastes which contain the active substance together with the usual excipients and adjuvants such as starch, cellulose powder, talc, magnesium stearate, sugar, gelatin, calcium carbonate, finely distributed silicic acid, carboxymethyl cellulose and similar substances.

For parenteral administration, there may be used solutions, for example oily solutions, prepared using sesame oil, castor oil or synthetic triglycerides, optionally with the addition of Tokopherol as anti-oxidation agent and/or using surface-active substances such as sorbitane fatty acid ester. In addition, there may be used aqueous suspensions prepared with the use of ethoxylated sorbitane fatty acid esters, optionally with the addition of thickening agents such as polyethylene glycol or carboxymethyl cellulose.

The concentrations of the active substances of the invention in the preparations prepared therewith ae preferably in the range of from 2 to 20 % by weight; for the use as medicaments for humans, the concentrations of the active substances are preferably in the range of from 20 to 80% by weight.

The following Examples illustrate the invention:

EXAMPLE 1

5-Phenoxy-benzimidazole-2-methyl-carbaminate 156 g of S-methyl-thiourea-sulfate were dissolved in 200 ml of water and then 100 ml of chloroformic acid amethyl ester and 340 g of a 25% sodium hydroxide solution were added dropwise, while stirring, at a temperature of 5° to 10° C. After having stirred for 20 minutes, the reaction mixture was combined with 600 ml of water, 100 ml of glacial acetic acid and 102 g of 3,4-diamino-diphenyl aether in 600 ml of ethanol. Stirring was continued for 90 minutes at a temperature of 85° C, during which time methyl-mercaptan was separated. After having allowed the whole to cool and to stand overnight, the 5-phenoxy-benzimidazole-2-methyl-carbaminate that had formed was filtered off with suction, dissolved in 1 liter of hot glacial acetic acid and precipitated with 2 liters of methanol; the pure product which was obtained in a yield of 116 g was found to melt at 248° C (decomposition).

For preparing the 3,4-diamino-diphenyl ether used as starting material, 172.5 g of 5-chloro-2-nitro-aniline were heated for 4 hours under reflux in 500 ml of dimethylformamide with 94 g of phenol in the presence of 150 g of anhydrous potassium carbonate. After cooling, the reaction mixture was diluted with 1000 ml of water, the 3-amino-4-nitro-diphenyl ether that had precipitated was filtered off with suction and purified by recrystallization from isopropanol. Yield: 100 g; melting point: 142° C.

103 g of the 3-amino-4-nitro-diphenyl ether so obtained were hydrogenated in 800 ml of dimethylformamide with Raney nickel under a pressure of 100 atmospheres gauge at room temperature, the catalyst was then removed by filtration and the solution was evaporated under reduced pressure. The 3,4-diamino-diphenyl ether that had formed was obtained in the form of a sirupy mass which was dissolved in ethanol and used in the reaction as described above.

EXAMPLES 2 – 30

The following compounds were prepared in analogous manner:

2. From 3-amino-4-nitro-4'-chloro-diphenyl ether (melting point 135° C) via the 3,4-diamino-4'-chloro-diphenyl ether, the 5-(4-chloro-phenoxy)-benzimidazole-2-methyl-carbaminate melting at 197° C.

3. From 3-amino-4-nitro-3'-chloro-diphenyl ether (melting point 114° C) via the 3,4-diamino-3'-chloro-diphenyl ether, the 5-(3-chloro-phenoxy)-benzimdazole-2-methyl-cabaminate melting at 230° C.

4. From 3-amino-4-nitro-2'-chloro-diphenyl ether (melting point 161°C) via the 3,4-diamino-2'-chloro-diphenyl ether, the 5-(2-chloro-phenoxy)-benzimidazole-2-methyl-carbaminate melting at 206°C.

5. From 3-amino-4-nitro-2',5'-dichloro-diphenyl ether (melting point 140°C) via the 3,4-diamino-2',5'-dichloro-diphenyl ether, the 5-(2,5-dichloro-phenoxy)-benzimidazole-2-methyl-carbaminate melting at 244°C.

6. From 3-amino-4-nitro-3',5'-dichloro-diphenyl ether (melting point 162° C) via the 3,4-diamino-3',5'-dichloro-diphenyl ether, the 5-(3,5-dichloro-phenoxy)-benzimidazole-2-methyl-carbaminate melting at 226° C.

7. From 3-amino-4-nitro-4'-bromo-diphenyl ether (melting point 129° C) via the 3,4-diamino-4'-bromo-diphenyl ether, the 5-(4-bromo-phenoxy)-benzimidazole-2-methyl-carbaminate melting at 248° C.

8. From 3-amino-4-nitro-3'-bromo-diphenyl ether (melting point 127° C) via the 3,4-diamino-3'-bromo-diphenyl ether, the 5-(3-bromo-phenoxy)-benzimidazole-2-methyl carbaminate melting at 232° C.

9. From 3-amino-4-nitro-2'-bromo-diphenyl ether (melting point 152° C) via the 3,4-diamino-2'-bromo-diphenyl ether, the 5-(2-bromo-phenoxy)-benzimidazole-2-methyl-carbaminate melting at 211° C.

10. From 3-amino-4-nitro-4'-methyl-diphenyl ether (melting point 128° C) via the 3,4-diamino-4'-methyl-diphenyl ether, the 5-(4-methyl-phenoxy)-benzimidazole-2-methyl-carbaminate melting at 251° C.

11. From 3-amino-4-nitro-3'-methyl-diphenyl ether (melting point 110° C) via the 3,4-diamino-3'-methyl-diphenyl ether, the 5-(3-methyl-phenoxy)-benzimidazole-2-methyl-carbaminate melting at 228° C.

12. From 3-amino-4-nitro-2'-methyl-diphenyl ether (melting point 137° C) via the 3,4-diamino-2'-methyl-diphenyl ether, the 5-(2-methyl-phenoxy)-benzimidazole-2-methyl-carbaminate melting at 216° C.

13. From 3-amino-4-nitro-4'-tert.butyl-diphenyl ether (melting point 94° C) via the 3,4-diamino-4'-tert.butyl-diphenyl ether, the 5-(4-tert. butyl-phenoxy)-benzimidazole-2-methyl-carbaminate melting at 250° C.

14. From 3-amino-4-nitro-2',4'-dimethyl-diphenyl ether (melting point 116° C) via the 3,4-diamino-2',4'-dimethyl-diphenyl ether, the 5-(2,4-dimethyl-phenoxy)-benzimidazole-2-methyl-carbaminate melting at 239° C.

15. From 3-amino-4-nitro-2'-chloro-4'-methyl-diphenyl ether (melting point 145° C) via the 3,4-diamino-2'-chloro-4'-methyl-diphenyl ether the 5-(2-chloro-4-methyl-phenoxy)-benzimidazole-2-methyl-carbaminate melting at 209 C.

16. From 3-amino-4-nitro-2'-chloro-6'-methyl-diphenyl ether (melting point 164° C) via the 3,4-diamino-2'-chloro-6'-methyl-diphenyl ether, the 5-(2-chloro-6-methyl-phenoxy)-benzimidazole-2-methyl-carbaminate melting at 300° C.

17. From 3-amino-4-nitro-3'-chloro-4'-methyl-diphenyl ether (melting point 139° C) via the 3,4-diamino-3'-chloro-4'-methyl-diphenyl ether, the 5-(3-chloro-4-methyl-phenoxy)-benzimidazole-2-methyl-carbaminate melting at 236° C.

18. From 3-amino-4-nitro-3'-chloro-6'-methyl-diphenyl ether (melting point 141° C) via the 3,4-diamino-3'-chloro-6'-methyl-diphenyl ether, the 5-(3-chloro-6-methyl-phenoxy)-benzimidazole-2-methyl-carbaminate melting at 218° C.

19. From 3-amino-4-nitro-3'-chloro-4'-carboethoxy-diphenyl ether (melting point 134° C) via the 3,4-diamino-3'-chloro-4'-carboethoxy-diphenyl ether, the 5-(3-chloro-4-carboethoxy-phenoxy)-benzimidazole-2-methyl-carbaminate melting at 194° C.

20. From 3-amino-4-nitro-4'-chloro-2'-methyl-diphenyl ether (melting point 142° C), via the 3,4-diamino-4'-chloro-2'-methyl-diphenyl ether, the 5-(4-chloro-2-methyl-phenoxy)-benzimidazole-2-methyl-carbaminate melting at 230° C.

21. From 3-amino-4-nitro-4'-chloro-3'-methyl-diphenyl ether (melting point 135° C) via the 3,4-diamino-4'-chloro-3'-methyl-diphenyl ether, the 5-(4-chloro-3-methyl-phenoxy)-benzimidazole-2-methyl-carbaminate melting at 253° C.

22. From 3-amino-4-nitro-4'-chloro-3',5'-dimethyl-diphenyl-ether (melting point 158° C) via the 3,4-diamino-4'-chloro-3',5'-dimethyl--diphenyl ether, the 5-(4-chloro-3,5-dimethyl-phenoxy)-benzimidazole-2-methyl-carbaminate melting at 239° C.

23. From 3-amino-4-nitro-3',5'-bis-trifluoromethyl-diphenyl ether (melting point 129° C) via the 3,4-diamino-3',5'-bis-trifluoromethyl-diphenyl ether, the 5-(3,5-bis-trifluoromethyl-phenoxy)-benzimidazole-2-methyl carbaminate melting at 238° C.

24. From 3-amino-4-nitro-4'-methoxy-diphenyl ether (melting point 169° C) via the 3,4-diamino-4'-methoxy-diphenyl ether, the 5-(4-methoxy-phenoxy)-benzimidazole-2-methyl-carbaminate melting at 246° C.

25. From 3-amino-4-nitro-3'-methoxy-diphenyl ether (melting point 128° C) via the 3,4-diamino-3'-methoxy-diphenyl ether, the 5-(3-methoxy-phenoxy)-benzimidazole-2-methyl carbaminate melting at 203° C.

26. From 3-amino-4-nitro-2'-methoxy-diphenyl ether (melting point 130° C) via the 3,4-diamino-2'-methoxy-diphenyl ether, the 5-(2-methoxy-phenoxy)-benzimidazole-2-methyl-carbaminate melting at 212° C.

27. From 3-amino-4-nitro-4'-propoxy-diphenyl ether (oily) via the 3,4-diamino-4'-propoxy-diphenyl ether, the 5-(4-propoxy-phenoxy)-benzimidazole-2-methyl-carbaminate melting at 218° C.

28. From 3-amino-4-nitro-4'-isopropoxy-diphenyl ether (oily) via the 3,4-diamino-4'-isopropoxy-diphenyl ether, the 5-(4-isopropoxy-phenoxy)-benzimidazole-2-methyl-carbaminate melting at 208° C.

29. From 3-amino-4-nitro-4'-butoxy-diphenyl ether (oily) via the 3,4-diamino-4'-butoxy-diphenyl ether, the 5-(4-butoxy-phenoxy)-benzimidazole-2-methyl-carbaminate melting at 210° C.

30. From 3-amino-4-nitro-4'-iso-butoxy-diphenyl ether (oily) via the 3,4-diamino-4'-iso-butoxy-diphenyl ether, the 5-(4-isobutoxy-phenoxy)-benzimidazole-2-methyl-carbaminate melting at 198° C.

EXAMPLE 31

5-Phenoxy-benzimidazole-2-methyl-carbaminate 15.6 g of S-methyl-thiourea sulfate was dissolved in 20 ml of water, 10 ml of chloroformic acid methyl ester and 34 g of 25 % sodium hydroxide solution were added dropwise, while stirring, at a temperature in the range of from 5° to 15° C. Stirring was continued for 20 minutes and the reaction mixture was combined with 20 ml of glacial acetic acid, 100 ml of water, 23.6 g of 3,4-diamino-diphenyl ether hydrochloride and 8.5 g of sodium acetate and the mixture was then stirred for 1 hour at a temperature of 85° C, during which time methyl mercaptan separated. The isolation and purification of the 5-phenoxy-benzimidazole-2-methyl-carbaminate also obtained in Example 1 was effected as described in Example 1.

The hydrochloride of the 3,4-diamino-diphenyl ether used as starting material was obtained from the filtrate, from which the Raney nickel had been removed, as described in Example 1, paragraph 3, by evaporation, dissolution in methanol and acidification with alcoholic hydrochloric acid. The reaction mixture was concentrated, combined with isopropanol and the hydrochloride of 3,4-diamino-diphenyl ether that had separated was filtered off with suction. After recrystallization from water, the hydrochloride was found to have a decomposition point of 200° C.

EXAMPLE 32

5-Phenoxy-benzimidazole-2-butylcarbaminate

The process was carried in a manner analogous to that described in Example 31, but using 13.7 g of chloroformic acid butyl ester instead of the chloroformic acid methyl ester. The yield of 5-phenoxy-benzimidazole-2-butyl-carbaminate was 7.5 g; melting point 188° C.

EXAMPLE 33

5-Phenoxy-6-chloro-benzimidazole-2-methyl-carbaminate 42.7 g of S-methyl-thiourea sulfate in 65 ml of water were combined, while stirring, at 5° – 15° C, with 24.6 g of chloroformic acid methyl ester and then with 92 g of 25% sodium hydroxide solution. Stirring was continued for 20 minutes and the mixture was then combined with 120 ml of water, 32 ml of glacial acetic acid, 36 g of 3,4-diamino-6-chloro-diphenyl ether and 120 ml of alcohol. The whole was heated for 90 minutes to 85° C, during which time methyl-mercaptan separated. After cooling, the crude product was filtered off with suction, dissolved in 1.5 liter of glacial acetic acid and combined with 2 liters of methanol. Upon cooling, 30 g of 5-phenoxy-6-chloro-benzimidazole-2-methyl-carbaminate melting at 270° C were obtained.

For preparing the 3,4-diamino-6-chloro-diphenyl ether, 20.7 g of 4,5-dichloro-2-nitroaniline in 150 ml of dimethylformamide were boiled under reflux for 6 hours with 9.4 g of phenol in the presence of 14 g of anhydrous potassium carbonate. After having allowed the whole to cool, 150 ml of water were added, stirring was continued for 3 hours and the crude product was filtered off with suction. After recrystallization from a mixture of glacial acetic acid and methanol, 3-amino-4-nitro-6-chloro-diphenyl ether melting at 131° C was obtained.

41.5 g of the 3-amino-4-nitro-6-chloro-diphenyl-ether so obtained were hydrogenated in 300 ml of dimethylformamide with Raney nickel at normal pressure and 40° C. The filtrate obtained after removal of the catalyst was concentrated under reduced pressure. The remaining brown highly viscous mass, constituting the 3,4-diamino-6-chloro-diphenyl ether, was used for the reaction according to paragraph 1 without any purification.

EXAMPLES 34 – 36

In a manner analogous to that described in Example 33, the following products were prepared:

34. From 3-amino-4-nitro-6-chloro-4'-chloro-diphenyl ether (melting point 210° C) via the 3,4-diamino-6-chloro-4'-chloro-diphenyl ether, the 5-(4-chlorophenoxy)-6-chloro-benzimidazole-2-methyl-carbaminate melting at 305° C.

35. From 3-amino-4-nitro-6-chloro-3'-chloro-diphenyl-ether (melting point 126° C) via the 3,4-diamino-6-chloro-3'-chloro-diphenyl ether, the 5-(3-chlorophenoxy)-6-chloro-benzimidazole-2-methyl-carbaminate melting at 263° C.

36. From 3-amino-4-nitro-6-chloro-2'-chloro-diphenyl ether (melting point 167° C) via the 3,4-diamino-6-chloro-2'-chloro-diphenyl ether, the 5-(2-chlorophenoxy)-6-chloro-benzimidazole-2-methyl-carbaminate melting at 238° C.

EXAMPLE 37

5-(4-Hydroxy-phenoxy)-benzimidazole-2-methyl-carbaminate 66 g of S-methyl-thiourea sulfate in 170 ml of water were combined, at 5° to 15° C, while stirring, with 31 ml of chloroformic acid methyl ester and then with 140 g of 25% sodium hydroxide solution. After having stirred for 20 minutes, the mixture was combined with 275 ml of water, 48 ml of glacial acetic acid, 52.7 g of 3,4-diamino-4'-hydroxy-diphenyl ether and 275 ml of ethanol. The whole was heated for 2 hours under reflux, the crude product was filtered off with suction when cooled; after recrystallization, 33 g of 5-(4-hydroxy-phenoxy)-benzimidazole-2-methyl-carbaminate melting at 238° C were obtained.

For preparing the 3,4-diamino-4'-hydroxy-diphenyl ether used as starting material, 117 g of 4-hydroxy-anisole in 400 ml of dimethylformamide were reacted with 163 g of 5-chloro-2-nitro-aniline in the presence of 132 g of anhydrous potassium carbonate for 4 hours under reflux. After having allowed the reaction mixture to cool, it was diluted with 400 ml of water, the crude product was filtered off with suction; after recrystallization from methyl glycol, 151 g of 3-amino-4-nitro-4'-methoxy-diphenyl ether melting at 169° C were obtained.

100 g of the 3-amino-4-nitro-4'-methoxy-diphenyl ether so obtained were heated for 4 hours to the boiling temperature with 1 liter of 48% hydrobromic acid. A clear solution was formed in which a precipitate separated after a short period of time. After cooling it was filtered off with suction and recrystallized from a mixture of 250 ml of ethanol and 130 ml of water, whereby 60 g of the 3-amino-4-nitro-4'-hydroxy-diphenyl ether melting at 196° C were obtained.

60 g of the nitro-compound so obtained were hydrogenated in 400 ml of dimethylformamide with Raney nickel at a hydrogen pressure of 50 atmospheres gauge and room temperature. The catalyst was removed by filtration with suction and the filtrate was concentrated under reduced pressure. The crude 3,4-diamino-4'-hydroxy-diphenyl ether was then further reacted without any purification.

EXAMPLES 38 and 39

In a mannr analogous to that described in Example 37, the following products were prepared:

38. From 3-amino-4-nitro-3'-methoxy-diphenyl ether (melting point 128° C) via the 3-amino-4-nitro-3'-hydroxy-diphenyl ether (oily) and 3,4-diamino-3'-hydroxy-diphenyl ether, the 5-(3-hydroxy-phenoxy)-benzimidazole-2-methylcarbaminate melting at 197°C.

39. From 3-amino-4-nitro-2'-methoxy-diphenyl ether (melting point 130° C) via the 3-amino-4-nitro- 2'-hydroxy-diphenyl ether (melting point 134° C) and 3,4-diamino-2'-hydroxy-diphenyl ether, the 5-(2-hydroxy-phenoxy)-benzimidazole-2-methyl-carbaminate melting at 223° C.

EXAMPLE 40

5-Phenylmercapto-benzimidazole-2-methyl-carbaminate 20.9 g of S-methyl-thiourea were reacted as described in Example 1 in 27 ml of water with 13.5 ml of chloroformic acid methyl ester, 45.7 ml of 25% sodium hydroxide solution, 27 ml of glacial acetic acid, 100 ml of water and 29 g of 3,4-diamino-diphenyl-thioether. After recrystallization from a mixture of glacial acetic acid and methanol, 14 g of 4-phenylmercapto-benzimidazole-2-methyl-carbaminate melting at 233° C were obtained.

For preparing the 3,4-diamino-diphenyl-thioether used as starting material, 22 g of thiophenol were heated for 6 hours under reflux in 100 ml of dimethylformamide with 5-chloro-2-nitro-aniline in the presence of 30 g of anhydrous potassium carbonate. The whole was allowed to cool, 100 ml of water were added and the crude product was filtered off with suction. After recrystallization from isopropanol, 38 g of 3-amino-4-nitro-diphenyl-thioether melting at 112° C were obtained.

38 g of the 3-amino-4-nitro-diphenyl-thioether so obtained were added to a solution prepared by dissolving 180 g of crystalwater containing stannous chloride in 200 ml of glacial acetic acid and saturation with gaseous hydrochloric acid at room temperature. A precipitate separated after a short time. The solvent was then removed by distillation under reduced pressure and the residue was combined with ice and an excess of concentration sodium hydroxide solution. The oil that had separated was taken up in ether. After evaporation of the ether, the 3,4-diamino-diphenyl-thioether remained behind in the form of an oil which was used in the reaction without any purification.

We claim:

1. A pharmaceutical composition for combatting helminths consisting essentially of from 2 to 80% by weight of a 2-carbalkoxy-amino-benzimidazole-5(6)-phenyl ether of the formula (I)

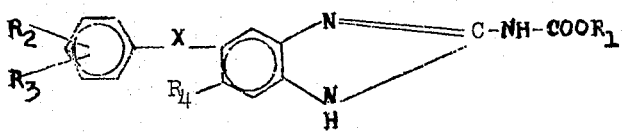

in which $R_1$ represents alkyl of 1 to 4 carbon atoms, $R_2$ and $R_3$ represent, independently of each other, hydrogen, hydroxyl, alkoxy of 1 to 4 carbon atoms halogen, trifluoromethyl, alkyl of 1 to 4 carbon atoms or carbalkoxy of 1 to 4 carbon atoms in the alkoxy group, $R_4$ represents hydrogen or chlorine and X represents oxygen or sulfur, wherein the same is in admixture with a pharmaceutically useful excipient.

2. A pharmaceutical composition as defined in claim 1, wherein the active substance is 5-phenoxy-benzimidazole-2-methyl-carbaminate.

3. A pharmaceutical composition as defined in claim 1, wherein the active substance is 5-(4-chloro-phenoxy)-benzimidazole-2-methyl-carbaminate.

4. A pharmaceutical composition as defined in claim 1, wherein the active substance is 5-(3-chloro-phenoxy)-benzimidazole-2-methyl-carbaminate.

5. A pharmaceutical composition as defined in claim 1, wherein the active substance is 5-(2-chloro-phenoxy)-benzimidazole-2-methyl-carbaminate.

6. A pharmaceutical composition as defined in claim 1, wherein the active substance is 5-(3-methoxy-phenoxy)-benzimidazole-2-methyl-carbaminate.

7. A pharmaceutical composition as dfined in claim 1, wherein the active substance is 5-phenylmercapto-benzimidazole-2-methyl-carbaminate.

8. A pharmaceutical composition as defined in claim 1, wherein the active substance is 5-(4-chloro-3,5-dimethyl-phenoxy)-benzimidazole-2-methyl carbaminate.

9. A pharmaceutical composition as defined in claim 1 wherein the compound of formula I is 5-(4-bromo-phenoxy)-benzimidazole-2-methyl-carbaminate.

10. A pharmaceutical composition as defined in claim 1 wherein the compound of formula I is 5-(3-methylphenoxy)-benzimidazole-2-methyl-carbaminate.

11. A pharmaceutical composition as defined in claim 1, wherein the active substance is 5-(2,5-dichlorophenoxy)-benzimidazole-2-methyl-carbaminate.

12. A pharmaceutical composition as defined in claim 1, wherein the active substance is 5-(3,5-dichlorophenoxy)-benzimidazole-2-methyl-carbaminate.

13. A pharmaceutical composition as defined in claim 1, wherein the active substance is 5-(4-bromo-phenoxy)-benzimidazole-2-methyl-carbaminate.

14. A pharmaceutical composition as defined in claim 1, wherein the active substance is 5-(2,4-dimethylphenoxy)-benzimidazole-2-methyl-carbaminate.

15. A pharmaceutical composition as defined in claim 1, wherein the active substance is 5-(2-chloro-4-methyl-phenoxy)-benzimidazole-2-methyl-carbaminate.

16. A pharmaceutical composition as defined in claim 1, wherein the active substance is 5-(3-chloro-4-carboethoxyphenoxy)-benzimidazole-2-methyl-carbaminate.

17. A pharmaceutical composition as defined in claim 1, wherein the active substance is 5-(3,5-bis-trifluoromethyl-phenoxy)-benzimidazole-2-methyl-carbaminate.

18. A pharmaceutical composition as defined in claim 1, wherein the active substance is 5-(3-chlorophenoxy)-6-chloro-benzimidazole-2-methyl-carbaminate.

19. A pharmaceutical composition as defined in claim 1, wherein the active substance is 5-(4-hydroxyphenoxy)-benzimidazole-2-methyl-carbaminate.

20. A method for oral or parenteral combatting of helminths by administering to a human, or a domestic animal, an effective amount from 0.5 to 50 mg per kg of body weight of a 2-carbalkoxy-amino-benzimidazole-5(6)-phenyl ether of the formula (I)

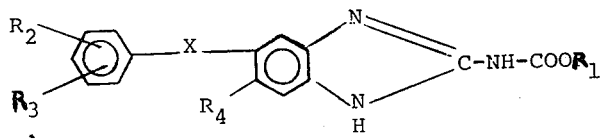

in which $R_1$ represents alkyl of 1 to 4 carbon atoms, $R_2$ and $R_3$ represent, independently of each other, hydrogen, hydroxyl, alkoxy of 1 to 4 carbon atoms, halogen, trifluoromethyl, alkyl of 1 to 4 carbon atoms or carbalkoxy of 1 to 4 carbon atoms in the alkoxy group, $R_4$ represents hydrogen or chlorine and X represents oxygen or sulfur.

21. The method of treatment defined in claim 20, wherein the active substance is 5-phenoxy-benzimidazole-2-methyl-carbaminate.

22. The method of treatment defined in claim 20, wherein the active substance is 5-(4-chlorophenoxy)-benzimidazole-2-methyl-carbaminate.

23. The method of treatment defined in claim 20, wherein the active substance is 5-(3-chlorophenoxy)-benzimidazole-2-methyl-carbaminate.

24. The method of treatment defined in claim 20, wherein the active substance is 5-(2-chlorophenoxy)-benzimidazole-2-methyl-carbaminate.

25. The method of treatment defined in claim 20, wherein the active substance is 5-(3-methoxyphenoxy)-benzimidazole-2-methyl-carbaminate.

26. The method of treatment defined in claim 20, wherein the active substance is 5-phenylmercapto-benzimidazole-2-methyl-carbaminate.

27. The method of treatment defined in claim 20, wherein the active substance is 5-(4-chloro-3,5-dimethylphenoxy)-benzimidazole-2-methyl-carbaminate.

28. The method of treatment defined in claim 20, wherein the active substance is 5-(4-bromophenoxy)-benzimidazole-2-methyl-carbaminate.

29. The method of treatment defined in claim 20, wherein the active substance is 5-(3-methylphenoxy)-benzimidazole-2-methyl-carbaminate.

30. The method of treatment defined in claim 20, wherein the active substance is 5-(2,5-dichlorophenoxy)-benzimidazole-2-methyl-carbaminate.

31. The method of treatment defined in claim 20, wherein the active substance is 5-(3,5-dichlorophenoxy)-benzimidazole-2-methyl-carbaminate.

32. The method of treatment defined in claim 20, wherein the active substance is 5-(4-bromophenoxy)-benzimidazole-2-methyl-carbaminate.

33. The method of treatment defined in claim 20, wherein the active substance is 5-(2,4-dimethylphenoxy)-benzimidazole-2-methyl-carbaminate.

34. The method of treatment defined in claim 20, wherein the active substance is 5-(2-chloro-4-methylphenoxy)-benzimidazole-2-methyl-carbaminate.

35. The method of treatment defined in claim 20, wherein the active substance is 5-(3-chloro-4-carboethoxyphenoxy)-benzimidazole-2-methyl-carbaminate.

36. The method of treatment defined in claim 20, wherein the active subsance is 5-(3,5-bis-trifluoromethylphenoxy)-benzimidazole-2-methyl-carbaminate.

37. The method of treatment defined in claim 20, wherein the active substance is 5-(3-chlorophenoxy)-6-chloro-benzimidazole-2-methyl-carbaminate.

38. The method of treatment defined in claim 20, wherein the active substance is 5-(4-hydroxyphenoxy)-benzimidazole-2-methyl-carbaminate.

* * * * *